US00PP12460P2

(12) United States Plant Patent
Heffner

(10) Patent No.: US PP12,460 P2
(45) Date of Patent: Mar. 12, 2002

(54) DOUBLE IMPATIENS PLANT NAMED 'BODDBLWHI'

(75) Inventor: Michael R. Heffner, Santa Barbara, CA (US)

(73) Assignee: John Bodger & Sons Co., South Elmonte, CA (US)

( * ) Notice: Subject to any disclaimer, the term of this patent is extended or adjusted under 35 U.S.C. 154(b) by 52 days.

(21) Appl. No.: 09/834,565

(22) Filed: Apr. 13, 2001

(51) Int. Cl.[7] ..... A01H 5/00
(52) U.S. Cl. ..... Plt./317
(58) Field of Search ..... Plt./317

(56) References Cited

U.S. PATENT DOCUMENTS

PP10,365 P * 4/1998 Cosner et al. ..... Plt./317

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Double Impatiens plant named 'Boddblwhi', characterized by its compact, mounded and outwardly spreading plant habit; freely branching habit; dark green leaves; large white-colored flowers; fully double flower form; freely flowering habit; and flowers positioned above the foliage.

1 Drawing Sheet

BACKGROUND OF THE INVENTION

The present Invention relates to a new and distinct cultivar of Double Impatiens plant, botanically known as *Impatiens walleriana*, and hereinafter referred to by the name 'Boddblwhi'.

The new Impatiens is a product of a planned breeding program conducted by the Inventor in Lompoc, Calif. The objective of the breeding program was to develop new compact Double Impatiens cultivars with fully double flowers, excellent branching, and attractive flower and foliage colors.

The new Impatiens originated from a cross made by the Inventor in October, 1999, of a proprietary *Impatiens walleriana* selection identified as 9IM1500-8, not patented, as the female, or seed parent, with a proprietary *Impatiens walleriana* selection identified as 9IM1813-2, not patented, as the male, or pollen parent. The cultivar 'Boddblwhi' was discovered and selected by the Inventor as a flowering plant within the progeny of the stated cross in a controlled environment in Lompoc, Calif.

Asexual reproduction of the new cultivar by terminal cuttings taken at Lompoc, Calif. since May, 2000, has shown that the unique features of this new Impatiens are stable and reproduced true to type in successive generations of asexual reproduction.

SUMMARY OF THE INVENTION

The following traits have been repeatedly observed and are determined to be the unique characteristics of 'Boddblwhi'. These characteristics in combination distinquish 'Boddblwhi' as a new and distinct cultivar:

1. Compact, mounded and outwardly spreading plant habit.
2. Freely branching habit.
3. Dark green leaves; densely foliated.
4. Large white-colored flowers.
5. Fully double flower form.
6. Freely flowering habit.

7. Flowers positioned above the foliage.

Plants of the new Impatiens differ primarily from plants of the female parent in flower form as plants of the female parent have semi-double flowers. Plants of the new Impatiens differ primarily from plants of the male parent in flower form as plants of the male parent have semi-double flowers.

The new Impatiens can be compared to the *Impatiens walleriana* cultivar 'BFP-7812', disclosed in U.S. Pat. No. 11,365. However, in side-by-side comparisons conducted in Lompoc, Calif., plants of the new Impatiens differ from plants of the cultivar 'BFP-7812' in the following characteristics:

1. Plants of the new Impatiens are more compact than plants of the cultivar 'BFP-7812'.
2. Plants of the new Impatiens have larger leaves than plants of the cultivar 'BFP-7812'.
3. Plants of the new Impatiens have larger flowers than plants of the cultivar 'BFP-7812'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph at the top of sheet comprises a side perspective view of a typical flowering plant of 'Boddblwhi' grown in a 15-cm container for about 14 weeks.

The photograph at the bottom of the sheet comprises a close-up view of typical developing flower buds, upper and lower surfaces of typical flowers, and upper and lower surfaces of typical leaves of 'Boddblwhi'.

DETAILED BOTANICAL DESCRIPTION

The cultivar 'Boddblwhi' has not been observed under all possible environmental conditions. The phenotype may vary somewhat with variations in environment such as temperature, light intensity, water status, and fertilizer rates without, however, any variance in genotype. The following observations, measurements and comparisons describe plants grown in Lompoc, Calif., under commercial practice during the summer and autumn in a polycarbonate-covered greenhouse with day temperatures about 24 to 29° C., night temperatures about 16 to 18° C. and light levels about 4,000 to 8,000 foot-candles. Unrooted cuttings were directly planted in 15-cm containers and grown for about 14 weeks.

In the following description, color references are made to The Royal Horticultural Society Colour Chart except where general terms of ordinary dictionary significance are used.

Botanical classification: *Impatiens walleriana* cultivar 'Boddblwhi'.

Parentage:

*Female parent.*—Proprietary *Impatiens walleriana* selection identified as 9IM1500-8, not patented.

*Male parent.*—Proprietary *Impatiens walleriana* selection identified as 9IM1813-2, not patented.

Propagation:

*Type cutting.*—Terminal cuttings.

*Time to initiate roots.*—About 10 to 14 days at 21° C.

*Time to produce a rooted cutting or liner.*—About 21 to 28 days at 21° C.

*Root description.*—Numerous and fine.

*Rooting habit.*—Freely branching.

Plant description:

*General appearance.*—Compact, mounded and outwardly spreading. Appropriate for 15-cm and larger containers.

*Growth and branching habit.*—Moderately vigorous and freely-branching with about 11 lateral branches at the base, dense and bushy growth. Pinching, that is, removal of the terminal apices, enhances branching.

*Crop time.*—About 8 to 9 weeks are required to produce a finished flowering plant from planting an unrooted cutting in a 15-cm pot.

*Plant height.*—About 16 cm.

*Plant diameter or spread.*—About 40 cm.

*Lateral branches.*—Length: About 16 cm. Diameter: About 9 mm. Internode length: About 2.75 cm. Texture: Smooth. Color: 145A.

*Foliage description.*—Leaves simple, alternate; generally symmetrical. Quantity: Densely foliated, about 18 leaves per lateral branch. Length: About 5.25 cm. Width: About 4 cm. Shape: Elliptic. Apex: Acute. Base: Attenuate. Margin: Serrate to crenate with ciliation. Texture: Glabrous, smooth. Venation pattern: Pinnate, arcuate. Color: Young and fully expanded foliage, upper surface: 147A. Young and fully expanded foliage, lower surface: 147B. Venation, upper and lower surfaces: 147B. Petiole: Length: About 3.75 cm. Diameter: About 3 mm. Color: 147D.

Flower description:

*Flower type and habit.*—Numerous and consistently double white-colored flowers. Freely and continuously flowering. Flower buds open similar to a rose in fullness; flowers rounded. Flowers arise from leaf axils. Usually about 26 flowers and flower buds per lateral branch. Flowers positioned above the foliage and typically face upright and/or outward. Flowers last about 5 to 7 days under greenhouse conditions. Flowers not persistent. Flowers not fragrant.

*Flowering season.*—Year-round under greenhouse conditions. In the garden, flowering is continuous from spring until fall.

*Flower size.*—Diameter: About 3.8 cm. Depth: About 2 cm.

*Flower buds.*—Rate of opening, from showing color to fully open flower: About 2 to 3 days. Length, at stage of showing color: About 1.3 cm. Diameter, at stage of showing color: About 9 mm. Shape: Ovoid. Color: 155C.

*Petals.*—Quantity/arrangement: About 28 per flower; imbricate. Length: About 2.2 cm. Width: About 2 cm. Shape: Cordate. Apex: Emarginate. Base: Acute. Margin: Entire. Texture: Velvety. Color: When opening, upper surface: 155D, iridescent. When opening, lower surface: 155D. Fully opened, upper surface: More white than 155D, iridescent. Fully opened, lower surface: 155D.

*Sepals.*—Quantity/arrangement: Five in a single whorl; one modified into an elongated spur; close to 145C. Calyx length: About 1.1 cm. Calyx diameter: About 9 mm. Shape: Elliptic. Apex: Broadly acute. Margin: Entire. Texture: Smooth. Color: Upper surface: 145D. Lower surface: 145C.

*Peduncles.*—Length: About 3.5 cm. Diameter: About 1.75 mm. Angle: About 45° to the lateral branch. Strength: Moderately strong. Color: 145D.

*Reproductive organs.*—None observed.

*Seed.*—None observed.

Disease pest resistance: Plants of the new Impatiens have not been observed to be resistant to pathogens and pests common to Impatiens.

It is claimed:

1. A new and distinct cultivar of Double Impatiens plant named 'Boddblwhi', as illustrated and described.

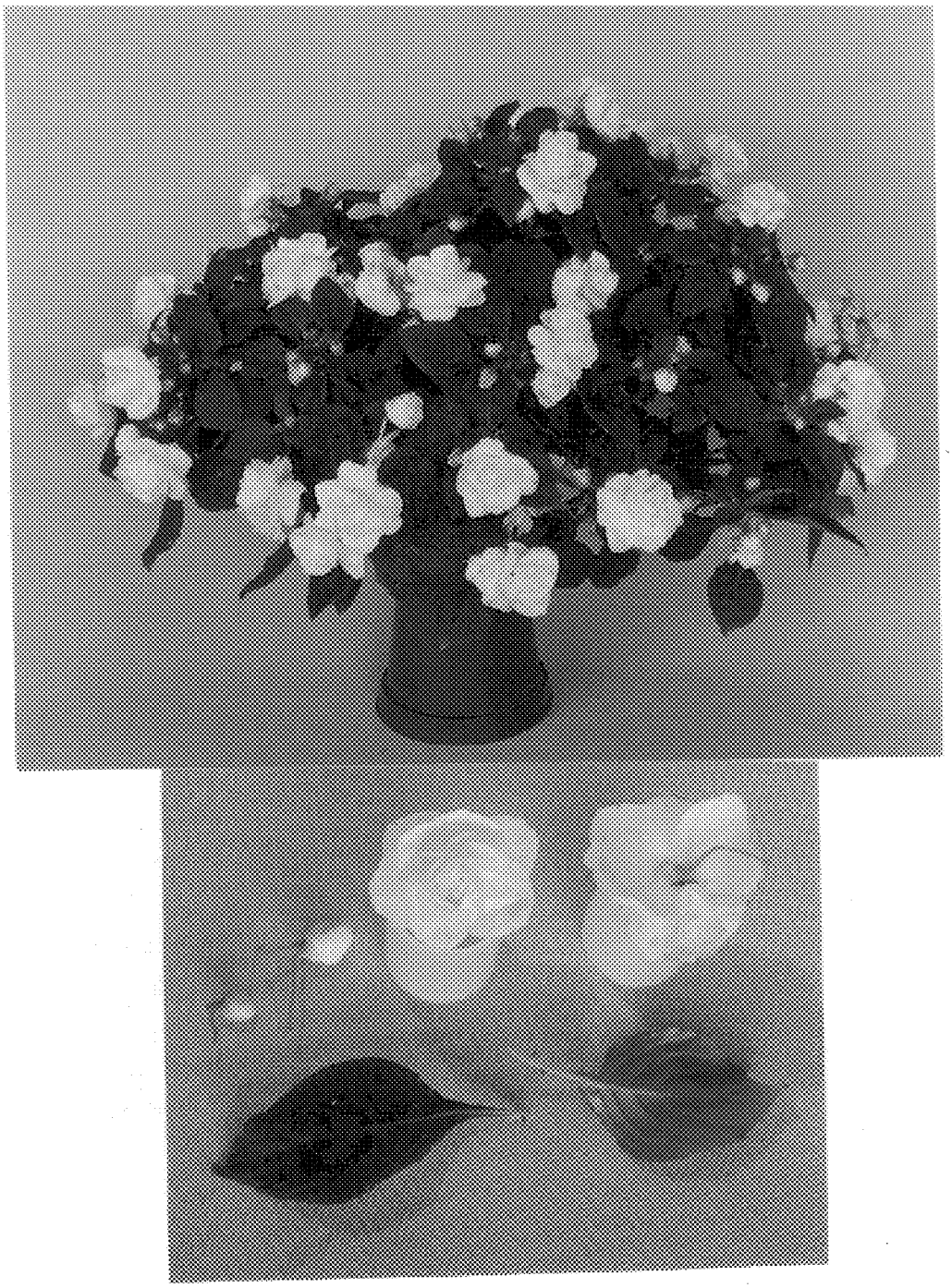

* * * * *